United States Patent
Stinnett, IV et al.

(10) Patent No.: US 12,217,842 B2
(45) Date of Patent: Feb. 4, 2025

(54) SYSTEMS AND METHODS FOR IMPROVING HEALTH SERVICES

(71) Applicant: Change Healthcare Holdings, LLC, Nashville, TN (US)

(72) Inventors: James Bryan Stinnett, IV, Nashville, TN (US); Margaret Grace Hoyt, Matthews, NC (US); Sabrina Nicole Kates, Mamaroneck, NY (US); Katherine Terry Coode, Nashville, TN (US); Samuel Becnel Rollenhagen, Morristown, NJ (US)

(73) Assignee: Change Healthcare Holdings, LLC, Nashville, TN (US)

( * ) Notice: Subject to any disclaimer, the term of this patent is extended or adjusted under 35 U.S.C. 154(b) by 712 days.

(21) Appl. No.: 17/354,173

(22) Filed: Jun. 22, 2021

(65) Prior Publication Data
US 2022/0406423 A1    Dec. 22, 2022

(51) Int. Cl.
*G16H 15/00* (2018.01)
*G16H 20/00* (2018.01)
*G16H 40/67* (2018.01)
*G16H 80/00* (2018.01)

(52) U.S. Cl.
CPC ............ *G16H 15/00* (2018.01); *G16H 20/00* (2018.01); *G16H 40/67* (2018.01); *G16H 80/00* (2018.01)

(58) Field of Classification Search
CPC ........ G16H 15/00; G16H 40/67; G16H 20/00; G16H 80/00
USPC ........................................................ 705/2–3
See application file for complete search history.

(56) References Cited

U.S. PATENT DOCUMENTS

| | | | | |
|---|---|---|---|---|
| 2014/0088991 | A1* | 3/2014 | Bakes | G16H 80/00 705/2 |
| 2016/0012198 | A1* | 1/2016 | Gainer, III | G06Q 40/08 705/2 |
| 2018/0308565 | A1* | 10/2018 | Pinter | G16H 10/60 |
| 2019/0096534 | A1* | 3/2019 | Joao | G16H 10/60 |

OTHER PUBLICATIONS

Krauss JC, Sahai V, Kirch M, Simeone DM, An L. Pilot Study of Personalized Video Visit Summaries for Patients With Cancer. JCO Clin Cancer Inform. 2018;2:1-8. doi:10.1200/CCI.17.00086 (Year: 2018).*

\* cited by examiner

*Primary Examiner* — Joy Chng
(74) *Attorney, Agent, or Firm* — MARSHALL, GERSTEIN & BORUN LLP

(57) ABSTRACT

A system for health services is provided. When a provider partners with the system the provider is assisted with the creation of an introduction video explaining their practice. The provider may also be assisted in the creation of videos that correspond to the top conditions or diseases treated by the provider as well as the top medicines that are prescribed. When a patient schedules a health service, the patient is initially provided the introduction video for the provider. During the health service, the system collects the health data entered or spoken by the provider. Based on the monitored data, the system automatically recommends relevant videos or content that may be included in a report for the patient. After the health service is completed, the system may further assist the provider in creating a video that explains the diagnosis and recommended treatment regiments.

20 Claims, 9 Drawing Sheets

200

300

400

500

600

US 12,217,842 B2

SYSTEMS AND METHODS FOR IMPROVING HEALTH SERVICES

BACKGROUND

Telehealth is becoming an increasing popular way for patients to consult with their medical providers without leaving their homes. It has numerous advantages over in-person consultations for both the medical provider and the patients including flexible scheduling and lower costs. However, some patients are reluctant to use telehealth services because of a perception that such services are cold, impersonal, or of a lower quality than traditional in-person health services. Furthermore, cost and time constraints placed on medical providers has reduced the overall amount of time that medical providers can spend with patients. This has led to a decrease in patient satisfaction with regards to in-person health services.

SUMMARY

In order to improve both in-person health services and telehealth services, a health service system is provided. When a medical provider partners with the service the medical provider is assisted with the creation of an introduction video that explains their medical practice. In addition, the medical provider may also be assisted in the creation of videos that correspond to the top conditions or diseases treated by the medical provider as well as the top medicines that are prescribed by the provider. When a patient schedules a health service (e.g., in-person or telehealth), the patient is initially provided the introduction video for the medical provider. During the health service, the system collects the health data entered or spoken by the medical provider into a medical health record associated with the patient including any diagnosis or treatment plans suggested by the medical provider. Based on the monitored data, the system automatically recommends relevant videos or content generated by the medical provider, as well as relevant content from third-parties, that may be included in a report for the patient. After the health service is completed, the system may further assist the medical provider in creating a custom video that explains the diagnosis and recommended treatment regiments. The system may then assist the medical provider in finalizing the report, including any generated video, and may provide the report to the patient through a portal.

In an embodiment, a method is provided. The method includes: generating a provider account for a medical provider by a health system; receiving first video content for the medical provider through a portal by the health system; generating an introduction video for the medical provider by the health system from the first video content; associating the introduction video with the medical provider by the health system; receiving a request for a health service with the medical provider from a patient through the portal by the health system, wherein the health service is associated with a time; providing the introduction video associated with the medical provider to the patient through the portal by the healthcare service before the time associated with the health service; and facilitating the requested health service with the patient and the medical provider at the time by the healthcare service.

In an embodiment, a method is provided. The method includes: facilitating a requested health service with a patient and a medical provider at a scheduled time by a health system; receiving health data related to the patient from the medial provider through a portal during the health service by the health system, wherein the health data comprises a diagnosis and a treatment plan; based on the health data, generating text for a patient report by the health system; based on the health data, identifying at least one video for the patient report by the health system; including the at least one video and the text in the patient report by the health system; and providing the patient report to the patient through the portal by the health system.

Additional advantages of the invention will be set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE DRAWINGS

The accompanying figures, which are incorporated herein and form part of the specification, illustrate a document attachment system and method. Together with the description, the figures further serve to explain the principles of the document attachment system and method described herein and thereby enable a person skilled in the pertinent art to make and use the document attachment system and method.

DETAILED DESCRIPTION

Figure 1:
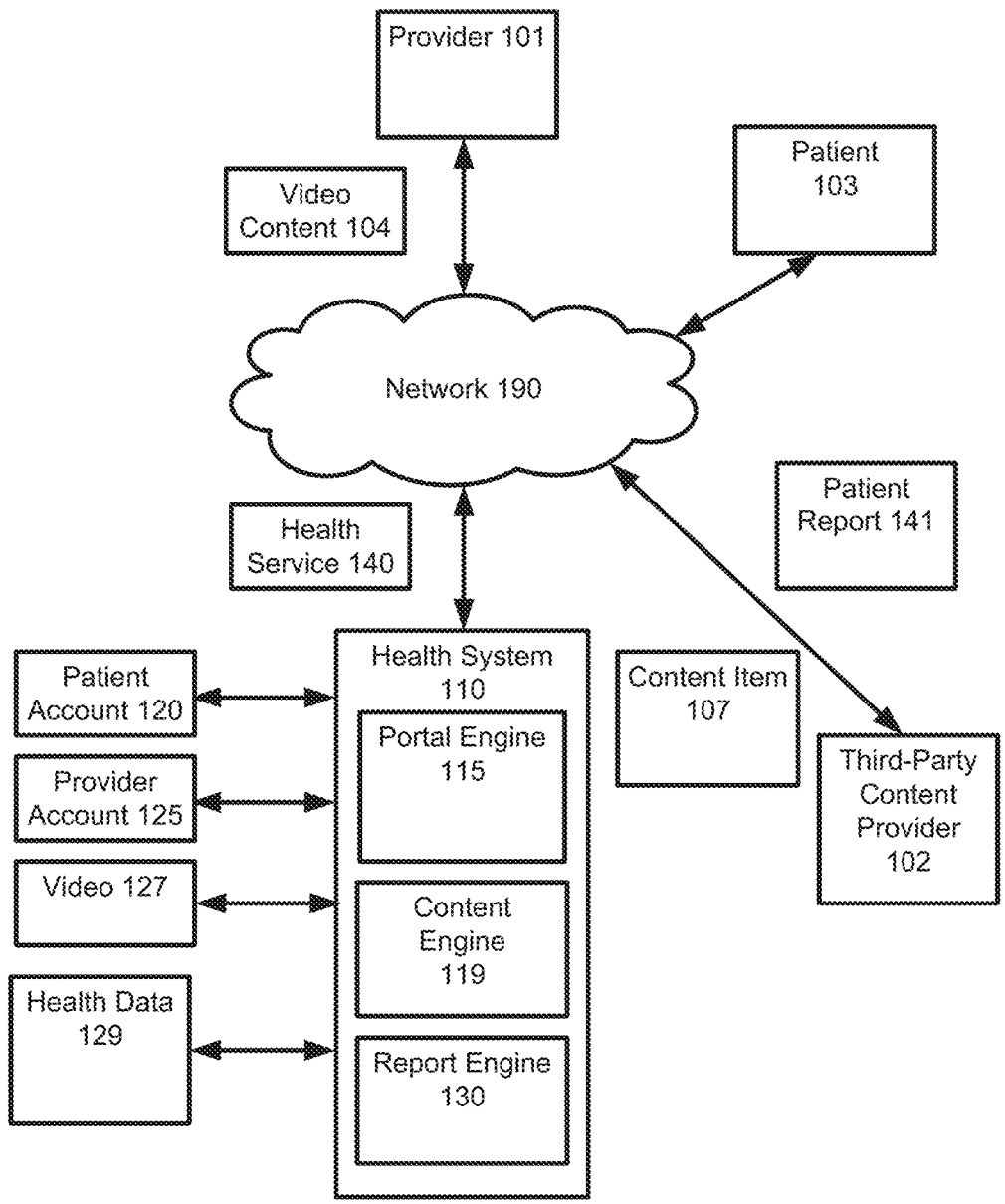
FIG. 1 is an example environment for providing health services.

FIG. 1 is an example environment 100 for providing health services 140. As shown, the environment 100 includes a health system 110, one or more providers 101, one or more patients 103, and one or more third-party content providers 102 in communication through a network 190. While only one provider 101, patient 103, health system 110, and third-party content provider 102 are shown; it is contemplated that there may be multiple providers 101, patients 103, health systems 110, and third-party content providers 102.

The provider 101 may be a healthcare provider such as a doctor, nurse, or nurse practitioner who provides health services 140. A health service 140 may include both traditional, in-person health or medical services, as well as telehealth services. A telehealth service (also referred to as a virtual heath service) is any health or medical service that is provided by a provider 101 to a patient 103 through the network 190. Typically, the patient 103 and the provider 101 will use a video conferencing application to conduct telehealth services, and the patient 103 and the provider 101 will discuss whatever health or medical issues that the patient 101 may have. The provider 101 may diagnose the patient 101, may provide one or more prescriptions, or may otherwise provide medical advice during the health service 140.

While telehealth services are popular due to decreased costs and flexible scheduling, many patients 101 view telehealth services as inferior to in-person health services due to a perceived lack of intimacy or familiarity with the provider 101 due to the virtual nature of the service. In addition, due to cost pressures (e.g., shorter appointment times) patient satisfaction with traditional in-person health services has also been decreasing. Accordingly, to increase patient 103 satisfaction with health services 140, the environment 100 includes the health system 110.

As shown, the health system 110 includes many components including a portal engine 115, a content engine 119, and a report engine 130. More or fewer components may be supported. Some or all of the components of the health system 110 may be implemented using one or more general purpose computing devices such as the computing device 900 illustrated in FIG. 9.

The portal engine 115 may provide a portal through which the patients 103 and providers 101 may interact with the health system 110 and provide and receive health services 140. Depending on the embodiment, the provider 101 and patient 103 may access the portal using one or more of a webpage or local application that is executed on a computing device (e.g., laptop, desktop, mobile phone, or tablet device) associated with the patient 103 or provider 101.

When the provider 101 first connects to the health system 110, the portal engine 115 may create a provider account 125 for the provider 101. The provider account 125 may uniquely identify the provider 101 and may include information about the provider 101 such as their name, contact information, schedule, medical specialty, education, papers written, insurance types accepted, and payment or price information. Other information may be included.

The portal engine 115 may similarly create a patient account 120 for each patient 103 that uses the health system 110. The patient account 120 may include information about the patient 101 such as their name, age, sex, and insurance information. The patient account 120 may further include medical or health information about the patient such as their medical history, medicines taken, and any allergies. Other information may be included.

The content engine 119 may assist the provider 103 with creating one or more videos 127. As will be discussed further below, some of these videos 127 may be provided to patients 101 before or after a health service 140.

One example video 127 is what is referred to as an introduction video 127. The purpose of the introduction video 127 is to provide introductory information about the provider 101 including their name, specialty, and philosophy. The introduction video 127 may also inform the patient 101 what they may expect from their health service 140. The introduction video 127 may help the patient 103 feel more connected to the provider 101, without the provider 101 having to take up additional time during the health service 140.

The portal engine 115 may allow the provider 101 to provide video content 104 using a camera associated with their mobile device or computer. The content engine 119 may receive the video content 104 and may use the video content 104 to create the introduction video 127. For example, the content engine 119 may provide video editing or processing tools that the provider 101 may use to edit or enhance (e.g., adjust color or contrast) the video content 104. The content engine 119 may also apply one or more overlays, watermarks, filters, or branding to the video content 104.

In some embodiments, the content engine 119 may provide a script that the provider 101 may use to create the video content 104 for the introduction video 127. For example, the content engine 119 may parse the information in the provider account 125 provided by the provider 101 and may insert the information (e.g., name, specialty, and, education) into a script template. Any method for generating a script may be used.

The content engine 119 may further help the provider generate videos 127 related to common diagnosis or medications that are prescribed by the provider. For example, if the provider 101 frequently prescribes a type of type of ointment, the content engine 119 may help the provider 101 create a video 127 that instructs patients 103 on how to apply the ointment. Depending on the embodiment, the content engine 119 may automatically recommend the videos 127 that the provider 101 should create based on an analysis of the provider's 101 practice or based on the videos 127 created by similar providers 101 (e.g., providers 101 that have the same specialty).

Figure 2:
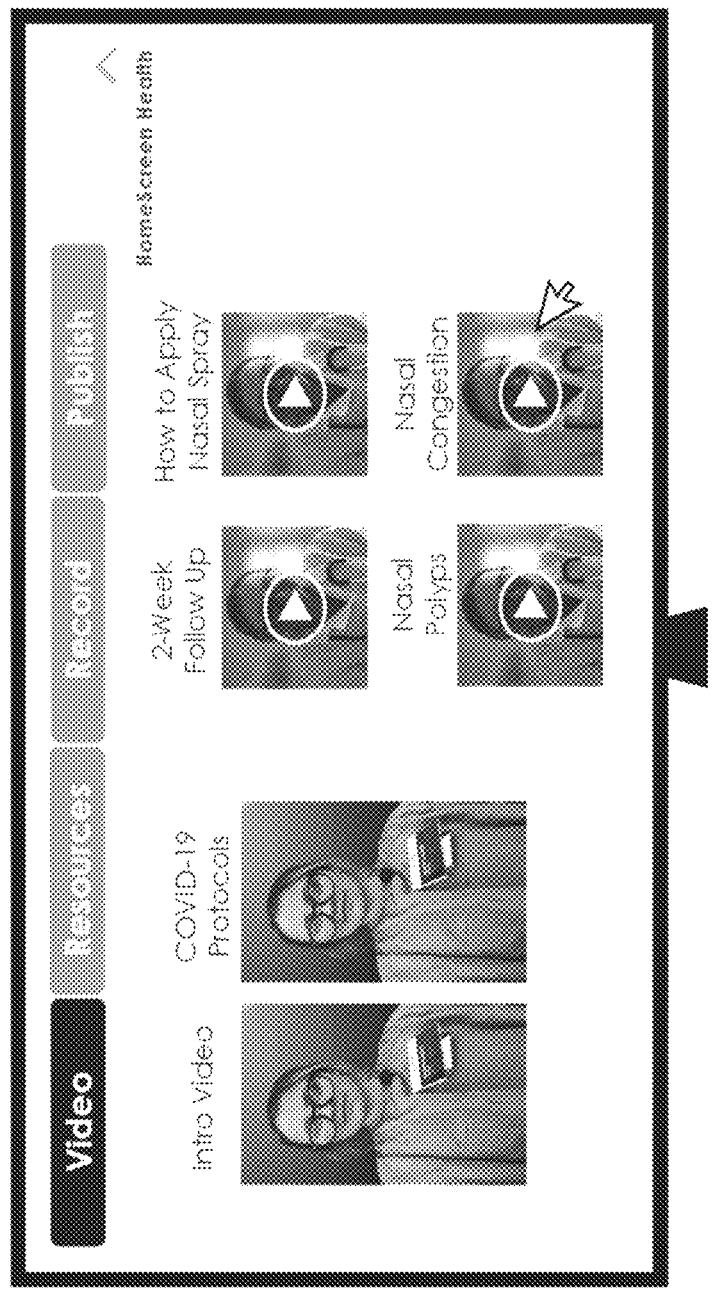
FIGS. 2-6 are illustrations of example graphical user interfaces for providing health services.

Continuing to FIG. 2 is an illustration of a graphical user interface 200 that may be part of the portal provided by the portal engine 115. As shown, the provider 101 has created several videos 127 including videos 127 titled "Intro Video", "COVID-19 Protocols", "2-Week Follow Up", "Nasal Polyps", "How to Apply Nasal Spray", and "Nasal Congestion." The provider 101 may use the user interface 200 to remove or add particular videos 127 to their provider account 125.

Returning to FIG. 1, when a patient 103 desires to schedule a health service 140 with a provider 101, the patient 103 may access the portal provided by the portal engine 115 using their patient account 120. The patient 103 may then search for a suitable provider 101 based on a variety of criteria such as specialty, cost, insurance accepted, availability, education, location, and patient reviews. Other criteria may be supported.

After selecting a provider 101 and date for a health service 140, the portal engine 115 may provide the patient 103 with a confirmation message along with the introduction video 127 (or link to the video 127) associated with the provider 101. Depending on the embodiment, the confirmation message and video 127 may be provided to the patient 103 through the portal and/or through an electronic messaging service such as e-mail or text message.

For telehealth services, before the time associated with the telehealth service is about to begin, the portal engine 115 may provide links to the portal or other application that may be used to conduct the telehealth service. The links may be provided to both the provider 101 and the patient 103. Depending on the embodiment, before the telehealth service begins the patient 103 may be shown the introduction video 127 along with any other videos 127 that have been selected by the provider 101.

For traditional in-person health services, the portal engine may similarly provide a link to the introduction video 127 (and other videos). The patient may view the videos before attending the in-person health service or may view the videos while waiting for their appointment in a waiting room, for example.

During the health service 140, the provider 101 may write or dictate information about the patient 103 through the portal. This information may include symptoms described by the patient 103, a diagnosis of the patient 103, and a treatment plan for the patient 103. The information collected for the patient 103 is referred to as health data 129 and may be stored or associated with the patient account 120 during or after the health service 140 has ended. The health data 129 may be stored by the portal engine 115 as an electronic medical record.

After the health service 140 is complete, the report engine 130 may help the provider 101 to generate a patient report 141 based on the health data 129. The purpose of the patient report 141 may be to explain to the patient 103 what was discussed during the health service 140 including the diagnosis and medicines that were prescribed. Based on the health data 129, including the notes made by the provider 101, the treatment plan, the diagnosis, or medicines prescribed, the report engine 130 may select one or more videos 127 associated with the provider 101 that may be relevant to the patient report 141. These videos 127 may be the videos that were generated by the provider 101 using the content engine 119.

Figure 3:
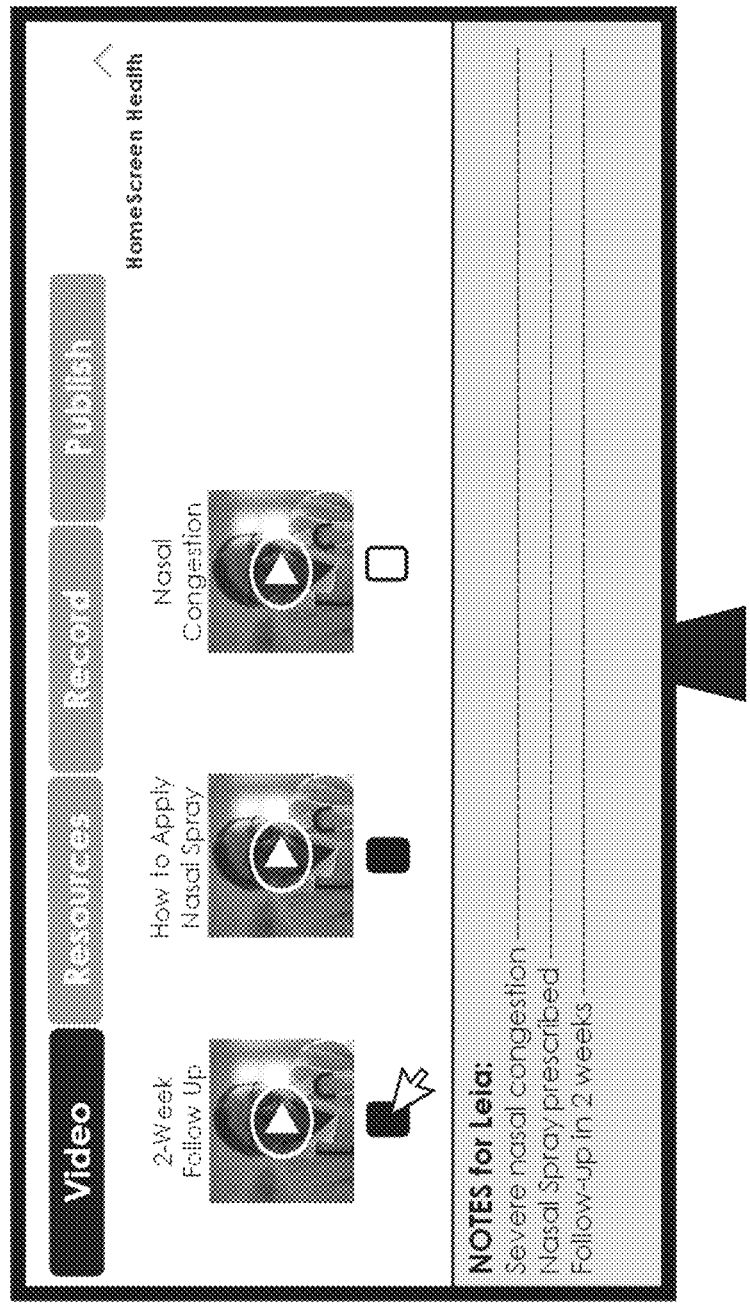

For example, referring to FIG. 3 is an illustration of a graphical user interface 300 that a provider 101 may be using to create a patient report 141. As shown in the "NOTES for Leia" section, during the health service 140 the provider 101 may have diagnosed the patient 103 with "Severe nasal congestion", may have prescribed "Nasal Spray", and may have recommended a "Follow-up in 2 weeks.". Based on this information, the report engine 130 has automatically identified relevant videos 127 and has displayed the relevant videos 127 in the graphical user interface 300. As shown, these include the video 127 titled "2-Week follow Up", "How to Apply Nasal Spray", and "Nasal Congestion." As shown, the provider 101 has selected to include the videos 127 "2-Week follow Up" and "How to Apply Nasal Spray" in the report 141.

Returning to FIG. 1, the report engine 130 may further select one or more content items 107 from one or more third-party content providers 102 for the patient report 141. The third-party content providers 102 may include drug manufacturers, insurance companies, publishers, researchers, and government agencies, for example. The content items 107 may include videos, papers, publications, or any other piece of content that might relate to a medication or a diagnosis. For example, a suitable content item 107 may include instructions for using a particular drug from the manufacturer, a list of side effects for a drug provided by the manufacturer, and a publication related to a particular disease published by an insurance company. Depending on the embodiment, the report engine 130 may select the content items 107 that may be relevant to the health data 129 provided by the provider 101 during the health service 140.

Note that the content items 107 may also include relevant content items 107 associated with the provider 101. For example, the continent items 107 may include a pamphlet that includes instructions from the provider 101 on how to apply a particular medicine.

Figure 4:
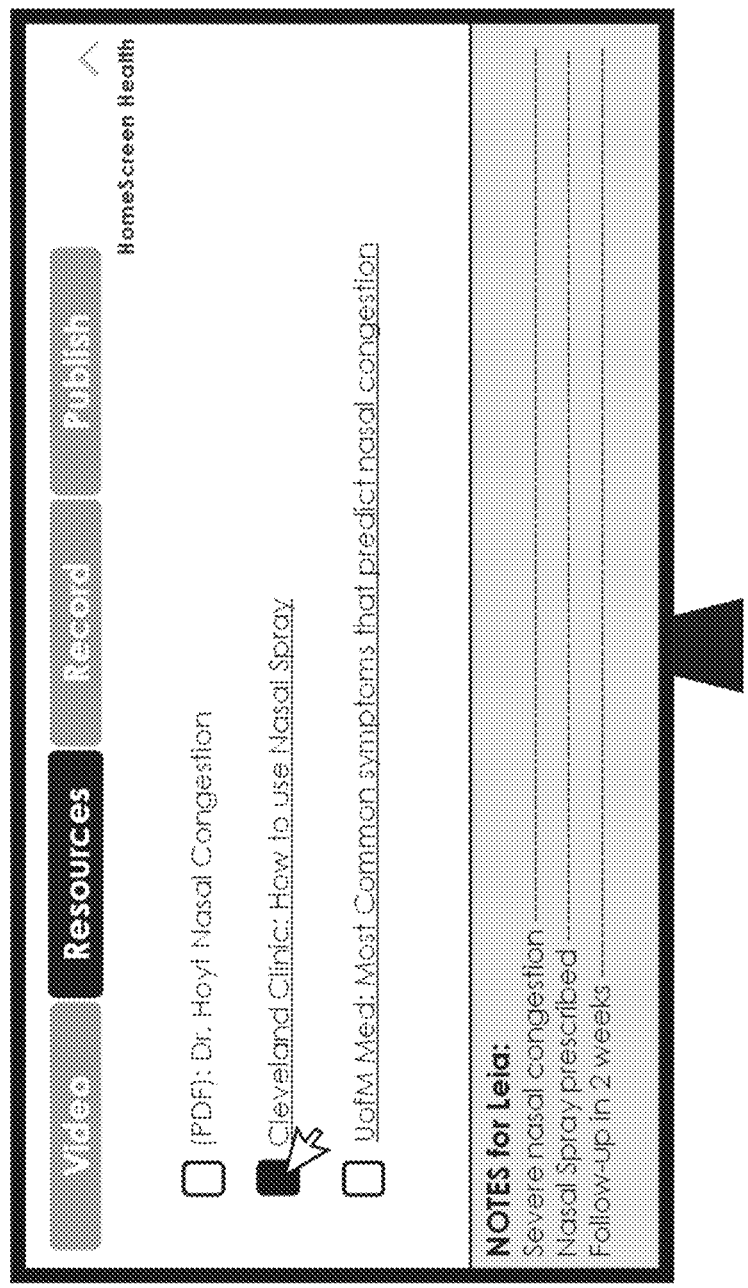

For example, referring to FIG. 4 is an illustration of a graphical user interface 400 that a provider 101 may be using to select content items 107 for a patient report 141. Continuing the example from FIG. 3, the report engine 130 may have recommended several content items 107 based on the health data 129 found in the "NOTES for Leia" section. As shown, the content items 107 include an article titled "(PDF): Dr. Hoyt Nasal Congestion", an articled titled "Cleveland Clinic: How to use Nasal Spray", and an article title "UofM Med: Most Common symptoms that predict nasal congestion." As shown, the provider 101 has selected to include the content item 107 titled "Cleveland Clinic: How to use Nasal Spray" in the report 141.

Returning to FIG. 1, the report engine 130 may further assist the provider 101 in creating a report video 127 for the patient report 141. The report video 127 may be a video 127 that meant to explain or summarize the outcome of the health service 140 to the patient 103. The report engine 130 may assist the provider 101 in generating the report video 127 using the portal similarly as described above for the content engine 119.

Figure 5:
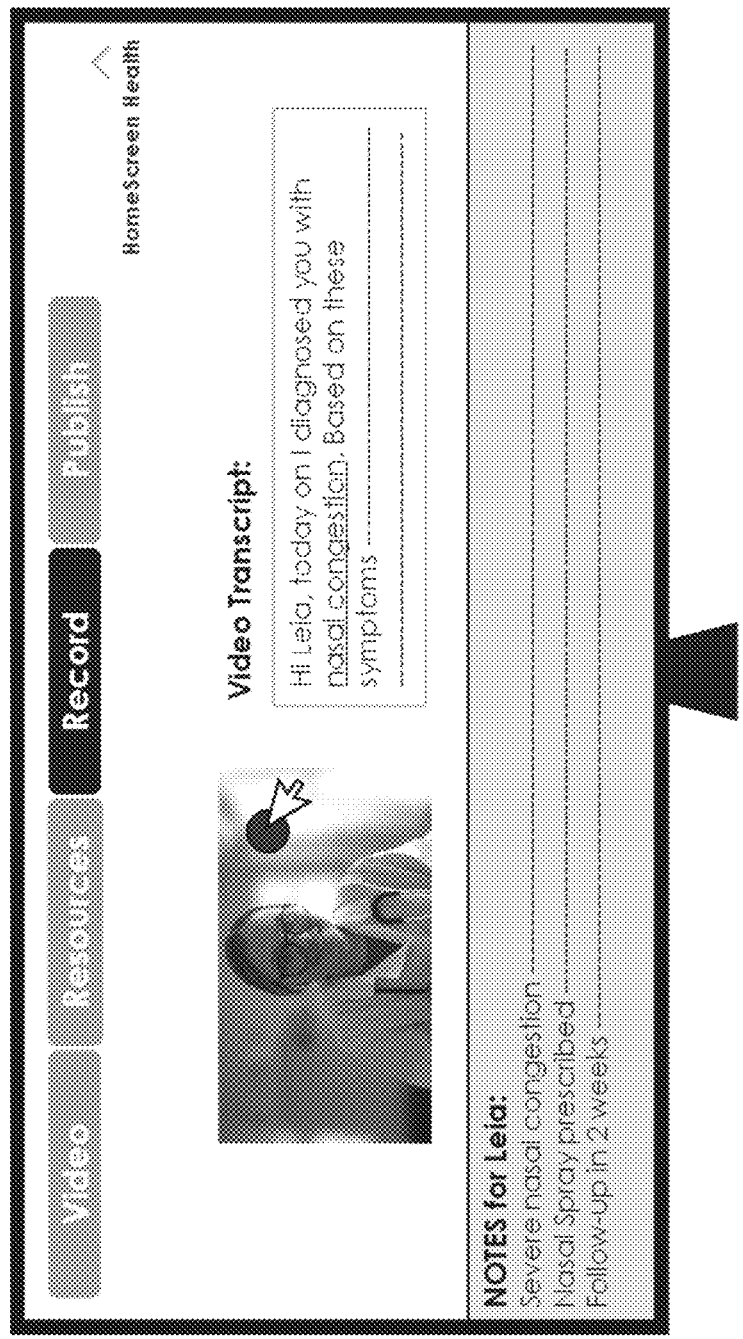

For example, referring to FIG. 5 is an illustration of a graphical user interface 500 that a provider 101 may be using to create a report video 127 for a patient report 141. Continuing the example from FIGS. 3 and 4, the report engine 130 may have generated a transcript for the video 127 based on the health data 129 entered into the "NOTES for Leia" section of the graphical user interface. As shown, the provider 101 is selecting a button that will cause the report engine 130 to begin recording the report video 127. The provider 101 may then speak the text of the transcript while the report video 127 is recorded.

Returning to FIG. 1, after the provider 101 has selected the videos 127 and content items 107 for the patient report 141, the provider 101 may publish the report 141 to the portal. The patient 103 may then use the portal to view the patient report 141. The portal engine 115 may then schedule any necessary follow-up appointment with the provider 101 for the patient 103.

Figure 6:
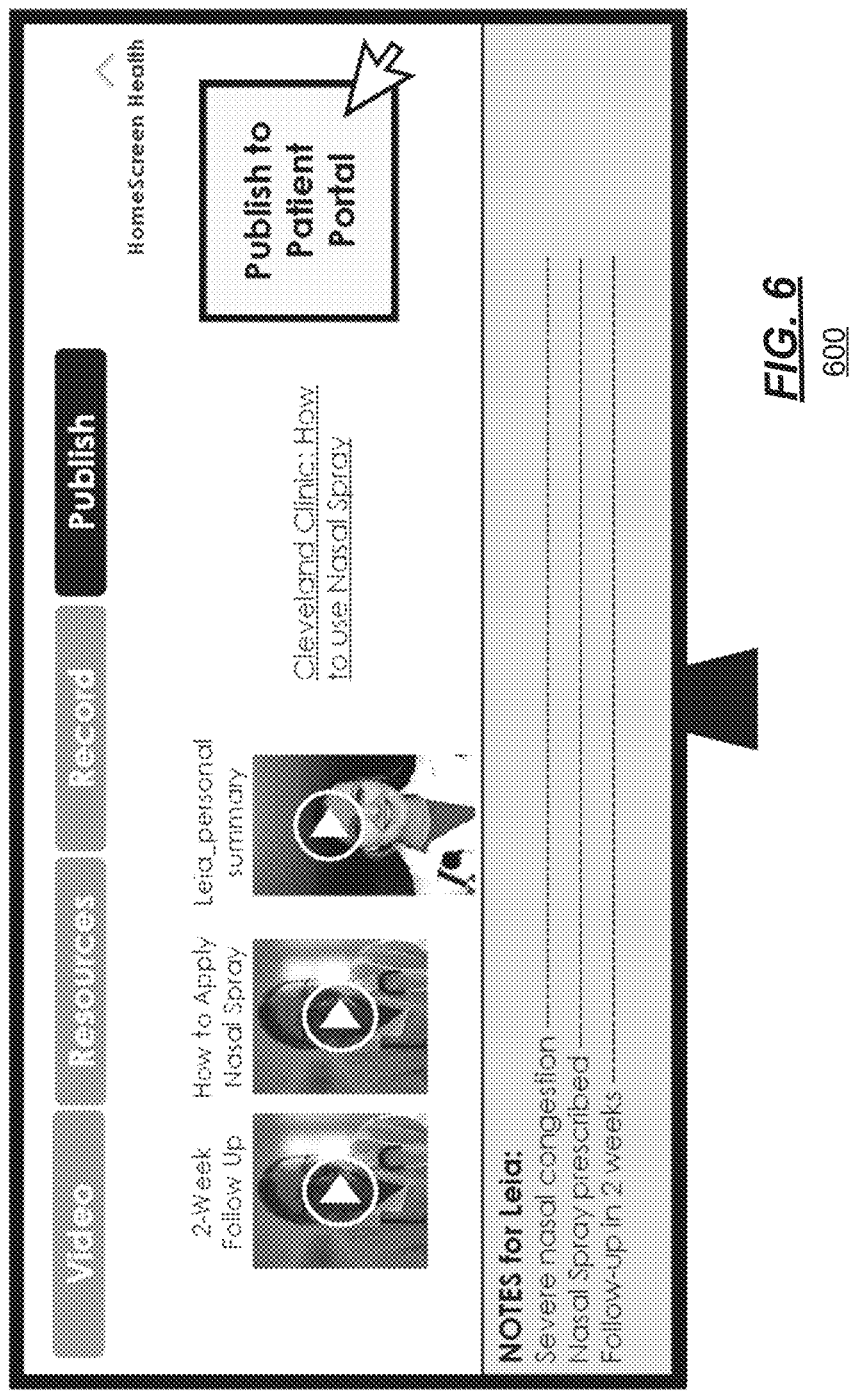

For example, referring to FIG. 6 is an illustration of a graphical user interface 600 that a provider 101 may be using to finalize and publish a patient report 141. Continuing the example from FIGS. 3, 4, and 5, the provider 101 can view the various videos 127 and content items 107 that the provider 101 has selected for the report 141. The provider 101 can add additional videos 127 and content items 107 to the report 141 or can remove videos 127 and content items 107 from the report 141. Once the provider 103 is satisfied with the report 141, they can publish the report 141 to the portal by selecting the button labeled "Publish to Patient Portal."

Figure 7:
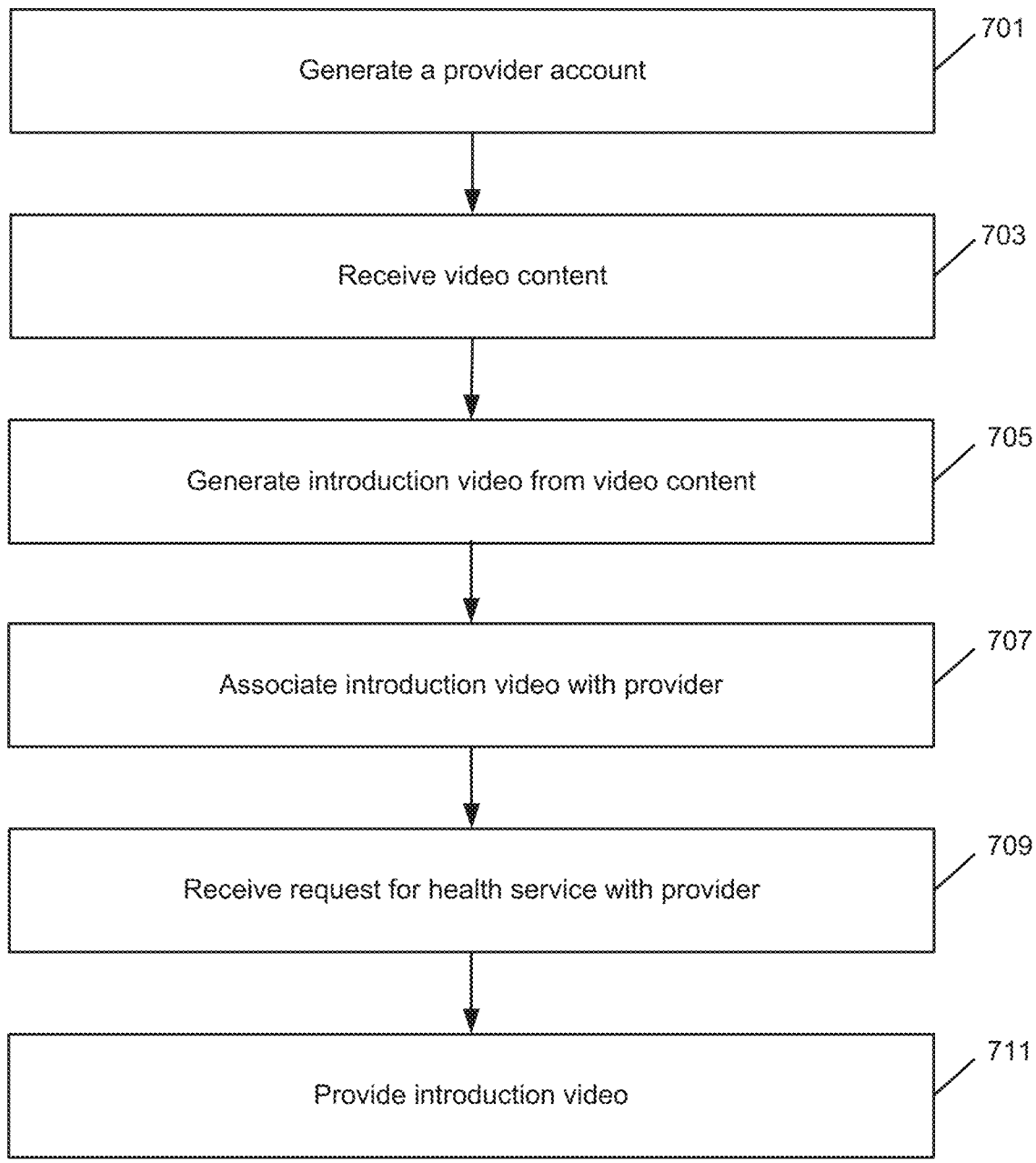
FIG. 7 is an illustration of a method for setting up a provider account and for creating an introduction video for a provider.

FIG. 7 is an illustration of a method 700 for setting up a provider account and for creating an introduction video for a provider. The method 700 may be implemented by the health system 110.

At 701, a provider account is generated. The provider account 120 may be created by the portal engine 115 of the health system 110. The provider account 125 may allow a provider 101 (e.g., a doctor) to provide one or more health services 140 to patients 103 either in-person or through a portal provided by the portal engine 115.

At 703, video content is received. The video content 104 may be received by the content engine 119 of the health system 110. The video content 104 may be for an introduction video that will played by the health system 110 to patients 103 before their health services 140 with the provider 101. Depending on the embodiment, the provider 101 may create the video content 104 using video and/or camera functionality associated with their computing device.

At 705, an introduction video is generated from the video content. The introduction video 127 may be generated by the content engine 119 from the video content 104 received from the provider 101. Depending on the embodiment, the content engine 119 may provide one or more editing tools to the provider 101 through the portal that the provider 101 may use to edit or modify the video content 104. The content engine 119 may automatically generate subtitles (in multiple languages) for the introduction video in multiple languages for accessibility purposes.

At 707, the introduction video is associated with the provider. The video 127 may be associated with the provider 101 by the content engine 119. The content engine 119 may associate the video 127 with the provider account 125 corresponding to the provider 101.

At 709, a request for a health service with the provider is received. The request may be received by the health system 110 through the portal from a patient 103. The request may be associated with a time that the health service 140 will take place.

At 711, the introduction video is provided. The introduction video may be provided by the health system to the patient 103 through the portal. The introduction video 127 may be provided (e.g., played) at anytime up until the health service 140 has begun. For example, the introduction video may be played to the patient 103 in the portal while the patient 103 waits for the health service 140 to begin.

Figure 8:
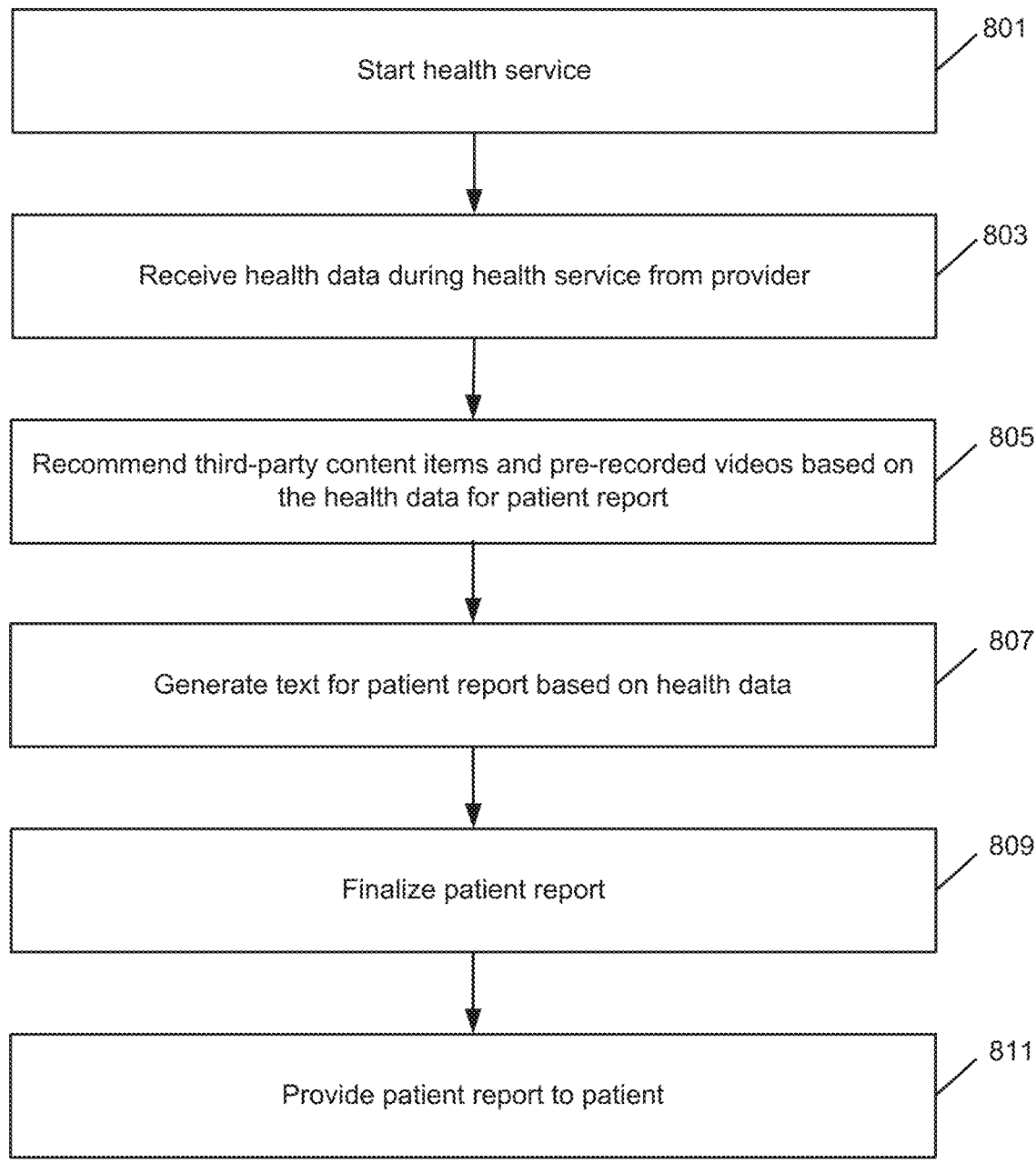
FIG. 8 is an illustration of a method for generating and providing a patient report to a patient after the completion of a health service.

FIG. 8 is an illustration of a method 800 for generating and providing a patient report to a patient after the completion of a health service. The method 800 may be implemented by the health system 110.

At 810, a health service 140 is started. The health service 140 may be started by the health system 110. The health service 140 may be a traditional in-person health service or may be a telehealth service. For telehealth services, the health service 140 may be provided through a portal and may be a video conference between a provider 101 and a patient 130.

At 820, health data is received. The health data 129 may be received by the portal engine 115 through the portal from the provider 101. The health data 129 may include notes taken by the provider 101 during the health service 140, any diagnosis made by the provider 101 during the health service 140, any medicine prescribed by the provider 101 during the health service, and any treatment plans made by the provider 101 during the health service 140.

At 805, one or more third-party content items and pre-recorded videos are recommended. The one or more third-party content items and pre-recorded videos may be recommended by the report engine 130 of the health system 110. The recommendations may be based on the health data 129. In some embodiments, the report engine 130 may select key words and phrases from the health data 129 and may identify third-party content items 107 and videos 127 based on the selected key words and phrases. For example, if the health data 129 includes a key word that is a particular disease or prescription drug, then the report engine 130 may recommend third-party content items 107 and videos 127 that are related to the particular disease or prescription drug. The videos 127 may be videos that were generated by the provider 101. The third-party content items 107 may be publications, websites, or videos that are provided by one or more third-party content providers 102 such as drug or insurance companies.

At 807, text is generated for the patient report 141. The text may be generated by the report engine 130 from the health data 129. The text may be meant to summarize what was discussed during the health service 140 and to explain and diagnosis or treatment plans that were made during the health service 140.

In addition to the text, the report engine 130 may further assist the provider 101 in creating a video 127 for the patient report 141. Like the text, the video 127 may summarize the service 140 and may discuss the diagnosis and treatment plans made during the service 140.

At 809, the patient report is finalized. The patient report 141 may be finalized by the provider 101 using the report engine 130. Prior to finalization, the provider 101 may remove or add videos 127 and content items 107 to the report 141 using the portal. The provider 101 may further edit the text that was generated by the report engine 130.

At 811, the patient report is provided to the patient. The report 141 may be provided to the patient 103 through the portal by the report engine 130.

Figure 9:
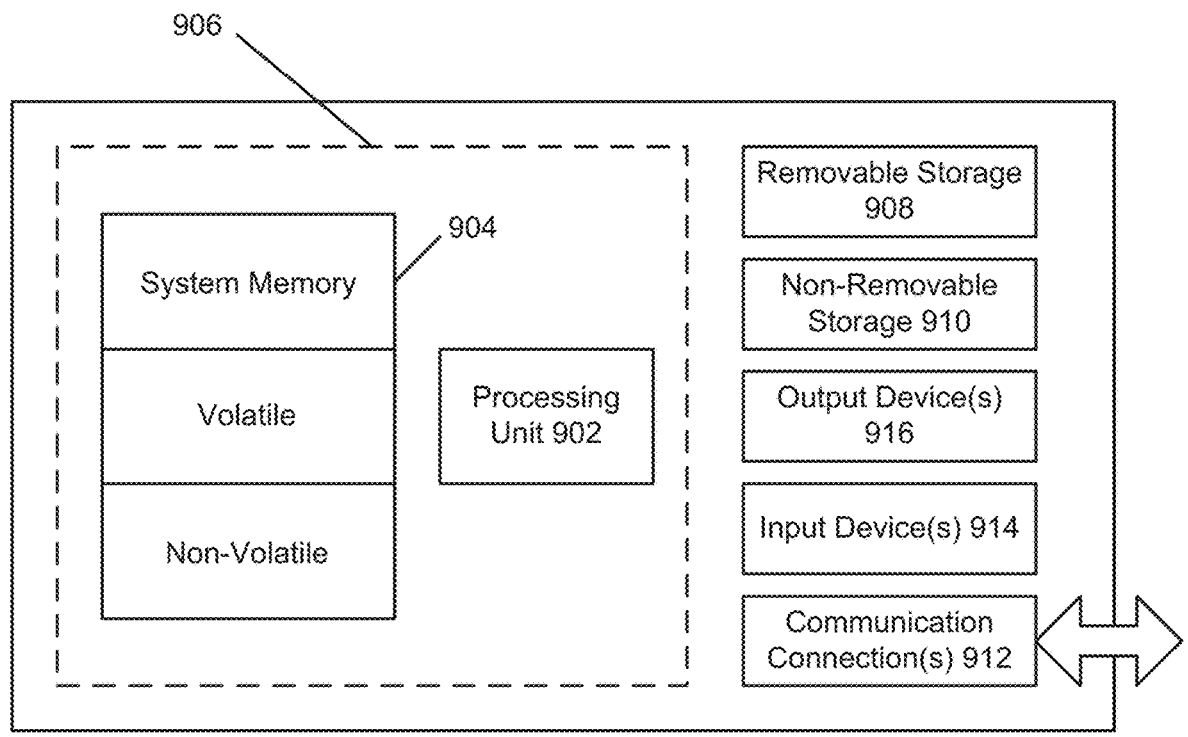
FIG. 9 shows an exemplary computing environment in which example embodiments and aspects may be implemented.

FIG. 9 shows an exemplary computing environment in which example embodiments and aspects may be implemented. The computing device environment is only one example of a suitable computing environment and is not intended to suggest any limitation as to the scope of use or functionality.

Numerous other general purpose or special purpose computing devices environments or configurations may be used. Examples of well-known computing devices, environments, and/or configurations that may be suitable for use include, but are not limited to, personal computers, server computers, handheld or laptop devices, multiprocessor systems, microprocessor-based systems, network personal computers (PCs), minicomputers, mainframe computers, embedded systems, distributed computing environments that include any of the above systems or devices, and the like.

Computer-executable instructions, such as program modules, being executed by a computer may be used. Generally, program modules include routines, programs, objects, components, data structures, etc. that perform particular tasks or implement particular abstract data types. Distributed computing environments may be used where tasks are performed by remote processing devices that are linked through a communications network or other data transmission medium. In a distributed computing environment, program modules and other data may be located in both local and remote computer storage media including memory storage devices.

With reference to FIG. 9, an exemplary system for implementing aspects described herein includes a computing device, such as computing device 900. In its most basic configuration, computing device 900 typically includes at least one processing unit 902 and memory 904. Depending on the exact configuration and type of computing device, memory 904 may be volatile (such as random access memory (RAM)), non-volatile (such as read-only memory (ROM), flash memory, etc.), or some combination of the two. This most basic configuration is illustrated in FIG. 9 by dashed line 906.

Computing device 900 may have additional features/functionality. For example, computing device 900 may include additional storage (removable and/or non-removable) including, but not limited to, magnetic or optical disks or tape. Such additional storage is illustrated in FIG. 9 by removable storage 908 and non-removable storage 910.

Computing device 900 typically includes a variety of computer readable media. Computer readable media can be any available media that can be accessed by the device 900 and includes both volatile and non-volatile media, removable and non-removable media.

Computer storage media include volatile and non-volatile, and removable and non-removable media implemented in any method or technology for storage of information such as computer readable instructions, data structures, program modules or other data. Memory 904, removable storage 908, and non-removable storage 910 are all examples of computer storage media. Computer storage media include, but are not limited to, RAM, ROM, electrically erasable program read-only memory (EEPROM), flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by computing device 900. Any such computer storage media may be part of computing device 900.

Computing device 900 may contain communication connection(s) 912 that allow the device to communicate with other devices. Computing device 900 may also have input device(s) 914 such as a keyboard, mouse, pen, voice input device, touch input device, etc. Output device(s) 916 such as a display, speakers, printer, etc. may also be included. All these devices are well known in the art and need not be discussed at length here.

It should be understood that the various techniques described herein may be implemented in connection with hardware components or software components or, where appropriate, with a combination of both. Illustrative types of hardware components that can be used include Field-programmable Gate Arrays (FPGAs), Application-specific Integrated Circuits (ASICs), Application-specific Standard Products (ASSPs), System-on-a-chip systems (SOCs), Complex Programmable Logic Devices (CPLDs), etc. The methods and apparatus of the presently disclosed subject matter, or certain aspects or portions thereof, may take the form of program code (i.e., instructions) embodied in tangible media, such as floppy diskettes, CD-ROMs, hard drives, or any other machine-readable storage medium where, when the program code is loaded into and executed by a machine, such as a computer, the machine becomes an apparatus for practicing the presently disclosed subject matter.

Although exemplary implementations may refer to utilizing aspects of the presently disclosed subject matter in the context of one or more stand-alone computer systems, the subject matter is not so limited, but rather may be implemented in connection with any computing environment, such as a network or distributed computing environment. Still further, aspects of the presently disclosed subject matter may be implemented in or across a plurality of processing chips or devices, and storage may similarly be effected across a plurality of devices. Such devices might include personal computers, network servers, and handheld devices, for example.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A method comprising:
   generating, by one or more processors of a health system, a provider account for a medical provider, wherein the provider account includes information entered by the medical provider;
   generating, by the one or more processors of the health system, a script for an introduction video for the medical provider based on the information about the medical provider and a script template;
   receiving, by the one or more processors of the health system, first video content from the medical provider through a portal, wherein the first video content is generated by the medical provider using a computing device associated with the medical provider and the script for the introduction video;
   generating, by the one or more processors of the health system, the introduction video for the medical provider from the received first video content;
   associating, by the one or more processors of the health system, the introduction video with the provider account of the medical provider;
   receiving, by the one or more processors of the health system, a request for a health service with the medical provider from a patient through the portal, wherein the health service is associated with a time;
   providing, by the one or more processors of the health system, the introduction video associated with the provider account of the medical provider to the patient through the portal before the time associated with the health service; and
   facilitating, by the one or more processors of the health system, the requested health service with the patient and the medical provider at the time.

2. The method of claim 1, further comprising:
   receiving, by the one or more processors of the health system, health data related to the patient from the medical provider through the portal during the health service, wherein the health data comprises a diagnosis and a treatment plan;
   based, by the one or more processors of the health system, on the health data, generating a patient report for the patient; and
   after the health service has ended, providing, by the one or more processors of the health system, the patient report to the patient through the portal.

3. The method of claim 2, further comprising:
   after the health service has ended, receiving, by the one or more processors of the health system, second video content for the medical provider through the portal, wherein the second video content is related to the health data;
   generating, by the one or more processors of the health system, a report video for the patient from the second video content; and
   providing, by the one or more processors of the health system, the report video with the patient report to the patient through the portal.

4. The method of claim 3, further comprising:
   based on the health data, generating, by the one or more processors of the health system, a script for the report video; and
   providing, by the one or more processors of the health system, the script for the report video to the medical provider through the portal, wherein the second video content is based in part on the provided script.

5. The method of claim 3, further comprising:
   generating, by the one or more processors of the health system, a transcript of the report video; and
   providing, by the one or more processors of the health system, the transcript with the report video, wherein the transcript is provided in a plurality of languages.

6. The method of claim 2, further comprising:
   based on the health data, recommending, by the one or more processors of the health system, a plurality of third-party content items to include in the patient report to the medical provider through the portal;
   receiving, by the one or more processors of the health system, a selection of at least one third-party content item of the plurality of third-party content items from the medical provider through the portal; and in response to the selection, including, by the one or more processors of the health system, the selected at least one third-party content item in the patient report.

7. The method of claim 1, wherein facilitating the requested health service with the patient and the medical provider at the time comprises establishing a video communication between the patient and the medical provider through the portal.

8. The method of claim 1, wherein the medical provider is a doctor or a nurse practitioner.

9. The method of claim 1, wherein generating, by the one or more processors of the health system, the introduction video for the medical provider from the received first video content comprises applying one or more overlays, watermarks, filters, or branding to the first video content.

10. The method of claim 1, wherein generating, by the one or more processors of the health system, the introduction video for the medical provider from the received first video content comprises providing one or more editing tools through the portal to edit the first video content into the introduction video.

11. A health system comprising:
one or more processors; and
one or more memories storing processor-executable instructions that, when executed by the one or more processors, cause the one or more processors to perform operations comprising:
generating a provider account for a medical provider, wherein the provider account includes information entered by the medical provider;
generating a script for an introduction video for the medical provider based on the information about the medical provider and a script template;
receiving first video content from the medical provider through a portal, wherein the first video content is generated by the medical provider using a computing device associated with the medical provider and the script for the introduction video;
generating the introduction video for the medical provider from the received first video content;
associating the introduction video with the provider account of the medical provider;
receiving a request for a health service with the medical provider from a patient through the portal, wherein the health service is associated with a time;
providing the introduction video associated with the provider account of the medical provider to the patient through the portal before the time associated with the health service; and
facilitating the requested health service with the patient and the medical provider at the time.

12. The system of claim 11, the one or more memories further storing processor-executable instructions that, when executed by the one or more processors, cause the one or more processors to perform operations comprising:
receiving health data related to the patient from the medical provider through the portal during the health service, wherein the health data comprises a diagnosis and a treatment plan;
based on the health data, generating a patient report for the patient; and
after the health service has ended, providing the patient report to the patient through the portal.

13. The system of claim 12, the one or more memories further storing processor-executable instructions that, when executed by the one or more processors, cause the one or more processors to perform operations comprising:
based on the health data, recommending a plurality of third-party content items to include in the patient report to the medical provider through the portal;
receiving a selection of at least one third-party content item of the plurality of third-party content items from the medical provider through the portal; and
in response to the selection, including the selected at least one third-party content item in the patient report.

14. The system of claim 12, the one or more memories further storing processor-executable instructions that, when executed by the one or more processors, cause the one or more processors to perform operations comprising:
after the health service has ended, receiving second video content for the medical provider through the portal, wherein the second video content is related to the health data;
generating a report video for the patient from the second video content; and
providing the report video with the patient report to the patient through the portal.

15. The system of claim 14, the one or more memories further storing processor-executable instructions that, when executed by the one or more processors, cause the one or more processors to perform operations comprising:
based on the health data, generating a script for the report video; and
providing the script for the report video to the medical provider through the portal, wherein the second video content is based in part on the provided script.

16. The system of claim 11, wherein facilitating the requested health service with the patient and the medical provider at the time comprises establishing a video communication between the patient and the medical provider through the portal.

17. The system of claim 11, wherein the health service is a telehealth service.

18. One or more non-transitory computer-readable media storing processor-executable instructions that, when executed by one or more processors, cause the one or more processors to perform operations comprising:
generating a provider account for a medical provider, wherein the provider account includes information entered by the medical provider;
generating a script for an introduction video for the medical provider based on the information about the medical provider and a script template;
receiving first video content from the medical provider through a portal, wherein the first video content is generated by the medical provider using a computing device associated with the medical provider and the script for the introduction video;
generating the introduction video for the medical provider from the received first video content;
associating the introduction video with the provider account of the medical provider;
receiving a request for a health service with the medical provider from a patient through the portal, wherein the health service is associated with a time;
providing the introduction video associated with the provider account of the medical provider to the patient through the portal before the time associated with the health service; and
facilitating the requested health service with the patient and the medical provider at the time.

19. The one or more non-transitory computer-readable media of claim 18, further storing processor-executable instructions that, when executed by the one or more processors, cause the one or more processors to perform operations comprising:
- receiving health data related to the patient from the medical provider through the portal during the health service, wherein the health data comprises a diagnosis and a treatment plan;
- based on the health data, generating a patient report for the patient; and
- after the health service has ended, providing the patient report to the patient through the portal.

20. The one or more non-transitory computer-readable media of claim 19, further storing processor-executable instructions that, when executed by the one or more processors, cause the one or more processors to perform operations comprising:
- after the health service has ended, receiving second video content for the medical provider through the portal, wherein the second video content is related to the health data;
- generating a report video for the patient from the second video content; and
- providing the report video with the patient report to the patient through the portal.

* * * * *